(12) United States Patent
Yadav et al.

(10) Patent No.: US 6,177,596 B1
(45) Date of Patent: Jan. 23, 2001

(54) HIGHLY ACIDIC MICROPOROUS SYNERGISTIC SOLID CATALYST AND ITS APPLICATIONS

(75) Inventors: Ganapati Dadasaheb Yadav; Jayesh Janardhan Nair, both of Mumbai; Vikas Narendra, Delhi, all of (IN)

(73) Assignee: Secretary, Dept. of Science and Technology, Government of India (IN)

( * ) Notice: Under 35 U.S.C. 154(b), the term of this patent shall be extended for 0 days.

(21) Appl. No.: 09/211,500

(22) Filed: Dec. 14, 1998

(30) Foreign Application Priority Data

Dec. 12, 1997 (IN) ........................................ 3591/97
Dec. 12, 1997 (IN) ........................................ 3592/97
Dec. 12, 1997 (IN) ........................................ 3593/97

(51) Int. Cl.$^7$ ........................... C07C 35/12; C07C 35/08; C07C 205/00; B01J 23/00; B01J 27/02
(52) U.S. Cl. ........................... 568/829; 568/828; 568/927; 502/349; 502/216; 502/217; 502/155; 502/159; 502/63; 502/64
(58) Field of Search ................... 502/349, 216, 502/217, 155, 159, 63, 64; 568/828, 829, 927

(56) References Cited

PUBLICATIONS

Yadav et al, Applied Catalysis A (1992), 90(2), 73–96.*

\* cited by examiner

Primary Examiner—Johann Richter
Assistant Examiner—J. Parsa
(74) Attorney, Agent, or Firm—Pendorf & Cutliff

(57) ABSTRACT

An active highly acidic microporous solid catalyst comprising sulphated metal oxide and at least one of carbon molecular sieve and/or heteropoly acid and having pore volume in the range of 0.1–0.2 m$^3$/g and pore size distribution in the range of 25–40 Å for use in acid catalized organic reactions which occur in the microporous range of the catalysts such as nitration of aromatic compounds, cyclization of terpenoids and more particularly relates to the preparation of modified sulphated zirconia catalysts. The invention also covers the process for producing the abovesaid solid catalyst and its use in producing isopulegol-rich in 1-isopulegol isomer from d-citronellal and in process for mononitration of aromatic compounds $C_6H_4R_1R_2$ wherein $R_1$=—$CH_3$, —$C_2H_5$, —Cl, —Br or —I and $R_2$=—H or —$CH_3$.

14 Claims, No Drawings

HIGHLY ACIDIC MICROPOROUS SYNERGISTIC SOLID CATALYST AND ITS APPLICATIONS

BACKGROUND OF THE INVENTION

1. Field of the Invention

The present invention relates to a process of preparing an improved solid catalyst for use in acid catalyzed organic reactions such as Friedel-Craft's reaction, nitration, cyclization and the method of manufacture of such a catalyst. This invention particularly relates to the preparation of catalysts for use in acid catalyzed organic reactions which occur in the microporous range of the catalysts such as nitration of aromatic compounds, cyclization of terpenoids and more particularly relates to the preparation of modified sulphated zirconia catalysts.

2. Description of the Related Art

Laszlo, P. and Pennetraeu, P., *J. Org. Chem.*, 52, 2407, 1987 have shown that copper nitrate supported K-10 clay gives the best o:p ratio of 1:7.5 so far reported for nitration of chlorobenzene. However, this catalyst did not give adequate para product, which is an important drug intermediate.

Shabtai, J., Lazar, R. and Biron, E., *J. Mol. Cat.*, 27, 35, 1984 have shown that depending on the alkali metal introduced in to the zeolite, the reaction yields either citronellol or isopulegol. With NaX, 85% isopulegol and 14% citronellol are obtained at 87% conversion of citronellal, while with CsX 92% citronellol is obtained at 77% conversion. However, this is rather attributed to a difference in pore dimension than to a difference in basicity.

Superacids as Catalysts

Superacids like K-10 clay, zeolites, silica-alumnia, sulphated metal oxides, like sulphated zirconia, etc. are substances known to have acidity higher than that of 100% sulphuric acid.

Preparation of Sulphated Zirconia (S-$ZrO_2$)

A variety of methods have been reported for the preparation of sulphated zirconia. These methods differ mainly in the type of precursor, type of precipitating agent, type of sulphating agent, method of impregnation, calcination temperature, etc.

The type of precursor for preparing sulphated zirconia plays a vital role in the final texture and hence, the performance of the catalyst. Various zirconium compounds such as $Zr(NO_3)_4$, $ZrCl_4$, zirconium isopropoxide, zirconyl chloride, zirconium oxychloride and sometimes, zirconia itself are used to prepare these catalysts. Various precipitating agents like aqueous ammonium hydroxide, and urea have been reported (Yamaguchi, T. and Tanabe, K., Mater. Chem. Phys., 16, 67, 1986). Sometimes hydrogen sulphide and sulphur dioxide are also used as sulphating agents. Amorphous zirconium hydroxide obtained by the alkaline hydrolysis of the zirconia precursor is usually sulphated before it is crystallized by thermal treatment. The sulphating species most commonly used are sulphuric acid and ammonium sulphate (Sohn, J. R. and Kim, H. W., J. Mol. Catal. 52, 361, 1989). The sulphated species is then thermally crystallized whereby it undergoes phase transformation, the tetragonal phase being stabilized as a result of sulphate incorporation.

Sulphated zirconia as such, prepared by co-precipitation of zirconium oxychloride with ammonia followed by sulphation, is a highly superacidic catalyst. Sulphated zirconia, prepared by sol-gel method, is also highly superacidic. However, co-precipitated zirconia is cost effective.

Many industrially important reactions have been studied for the use of sulphated zirconia because of its superacidic character. Some of these reactions are Friedel-Crafts alkylation, acylation, condensation, esterification, etherification, nitration, isomerization, cracking, dehydration, oligomerization, etc. But one of the major drawbacks of sulphated zirconia is that it is not a shape selective catalyst.

Carbon Molecular Sieves (CMS) and CMS Coated Catalysts

Carbon molecular sieves (CMS) are substances which have micro- or mesopores depending on the source and the method of preparation. They are mostly used in the separation of gases like nitrogen and oxygen gas from air, methane and ethane gas, etc. CMS are prepared from coal, by pyrolysis of precursor polymeric materials like polyacrylonitrile, phenol formaldehyde resin, polyvinylidene chloride, polyfurfuryl alcohol, polyvinyl alcohol, etc. or any combination of the above. CMS prepared by pyrolysis of polymers are found to be inert having absolutely no catalytic activity. The diffusivities of molecules through the ultramicroporous networks of CMS materials display a strong dependence on the critical kinetic diameter of the molecule. Hence the concept of coating carbon molecular sieves on superacids has been explored.

Foley, H. C., *Perspectives in Molecular Sieve Science*, American Chemical Society, 335, 1988, reports that the research groups of Walker and Trimm were the first to have investigated the reactant shape-selectivity of metal containing carbon molecular sieves. Trimm and Cooper (*Chem. Commun.*, 477, 1970; *J. Catal.*, 31, 287, 1973) and Schmitt and Walker (*Carbon*, 9, 791, 1971; *Carbon*, 10, 87, 1972), studied CMS/Pt catalysts for the shape selective hydrogenation of gas phase olefins. There were further developments in this field whereby a composite mixture of inorganic oxides (e.g., $SiO_2$, $TiO_2$, $ZrO_2$, $TiO_2$—$ZrO_2$, etc.) modified with CMS could be used as catalyst.

SUMMARY OF THE INVENTION

It is the basic objective of the present invention to provide carbon molecular sieve coated active highly acidic microporous solid catalyst, the pore dimension of which will favor the selective cyclizations and nitrations.

Another objective of the invention is to provide a process for producing tailor made carbon molecular sieve coated active highly acidic microporous solid catalysts for reaction such as mono- nitration with high para-selectivity, cyclization with high 1-isomer formation.

Yet further object of the present invention is directed to selecting the proper solid acid catalysts which would provide improved selectivity towards the formation of the desired products through selective cyclization and nitration.

Yet further object of the invention is directed to develop a novel composite catalyst by combining the activity of solid acid catalyst and pore selectivity of CMS.

Another objective of the present invention to provide an improved process for synthesis of 1-isopulegol by catalytic conversion of d-citronellal to 1-isopulegol which will provide or good yields of 1-isopulegol.

Yet another objective of the present invention is to provide a process for synthesis of 1-isopulegol from d-citronellal which will be simple, pollution free and safe to carry out and provide for improved yield of 1-isopulegol.

Yet another object of the present invention is directed to provide a process for ecofriendly and safe process of manufacture of 1-isopulegol and important medicinal compound such as 1-menthol from 1-isopulegol.

Further objective of the present invention to provide a process for selective nitration of aromatic compounds with increased para-selectivity.

Yet further object of the present invention is to provide for the selective synthesis of p-nitro compounds from aromatic compounds ($C_6H_5$—R, where R=—$CH_3$, —$C_2H_5$, —Cl, —Br, —I, etc.), using acetic anhydride and nitric acid utilizing an improved sulphated zirconia based catalyst.

DETAILED DESCRIPTION OF THE INVENTION

Thus according to one aspect of the present invention there is provided an active highly acidic microporous solid catalyst comprising sulphated metal oxide and at least one of carbon molecular sieve coated and optionally further including heteropoly acid and having pore volume in the range of 0.1–0.2 $m^3$/g and pore size distribution in the range of 25–40 Å.

In accordance with a preferred aspect of the invention the active highly acidic microporous solid catalyst comprise said sulphated metal oxide and atleast one of said carbon molecular sieve coated and optionally further including heteropoly acid and having BET surface area in the range of 60–165 $m^2$/g, pore volume in the range of 0.1 to 0.2 $m^3$/g, and pore size distribution in the range of 25–40 Å and d-spacing in the range of 1.5 to 3.75 Å for all the peaks.

According to another aspect of the invention there is provided the process for producing shape selective microporous solid catalysts comprising the steps of:

i. providing of the sulphated zirconia
ii. coating the sulphated zirconia with at least one of the carbon molecular sieve modifying agent/precursor selected from polyfurfuryl alcohol, phenol-formaldehyde resin, polyvinyl alcohol, polyacrylo nitrile, heteropoly acids with or without heteropoly acid and/or previously wetting the said sulphated zirconia with solvent.
iii. drying the sulphated zirconia between 100–150° C.
iv. calcining the carbon molecular sieve carbon molecular sieve precursor coated sulphated zirconia at temperature ranging up to 350° C. preferably 100–350° C. to thereby obtain the sulphated zirconia in the form of shape selective microporous solid catalyst.

The solvent used in step (ii) above for wetting the sulphated zirconia is selected from aliphatic, aromatic, cyclic or chlorinated hydrocarbons, aliphatic alcohols, aliphatic ketones. In the above process depending upon the precursor coating material used in step (ii) the calcining temperature varied. In particular, when the carbon molecular sieve precursor coating material in step (ii) above used is polyvinyl alcohol the calcination temperature in step (iv) is 100° C.–350° C. and when the precursor coating material in step (ii) above used includes heteropoly acid dodecatungstophosphoric acid then the calcination temperature in step (iv) is 200° C.–250° C.

The active catalytic phase of the CMS/S-$ZrO_2$ material of the present invention is the solid acid S-$ZrO_2$, which is a well known superacid catalyst whereas the CMS acts as a barrier for the bulkier molecules. The carbon molecular sieve of the present invention is synthesized from a precursor material. Examples of preferred precursor materials are polyacrylonitrile, phenol formaldehyde resin, polyvinylidene chloride, polyfurfuryl alcohol, polyvinyl alcohol or any combination of the above. A preferred method of forming the carbon molecular sieves used in the production of the CMS/S-$ZrO_2$ material of the present invention is the pyrolysis of polyvinyl alcohol. However, any known method of forming microporous carbon materials or carbon molecular sieves can be used in the production of CMS/S-$ZrO_2$ material of the present invention.

The carbon molecular sieve coated catalyst of the invention are adapted to utilize the active phases of the HPA/S-$ZrO_2$ material of the present invention are both the Bronsted acid sites of HPA and the Lewis acid sites of S-$ZrO_2$ whereby making them useful for nitration and cyclization reactions.

The process of present invention is for the preparation of catalysts of both the types, CMS/S-$ZrO_2$ and CMS/HPA/S-$ZrO_2$ catalysts.

In particular the process for preparation of the catalysts comprises:

preparation of zirconium hydroxide by conventional precipitation technique;

treating the zirconium hydroxide formed with sulphating agents such as sulphuric acid, ammonium sulfate, etc., calcining the reaction product at 200–700° C., to get sulphated zirconia;

mixing the sulphated zirconia (after pulverizing) and a solution of a carbon molecular sieve precursor material such as PVA dissolved in water, phenol-formaldehyde dissolved in acetone, with or without HPA dissolved in methanol, by incipient wetness technique to get precursor coated sulphated zirconia;

drying the carbon molecular sieve precursor coated sulphated zirconia at 100–150° C.;

treating the dry precursor coated sulphated zirconia at temperature equal to or less than that used in calcining step for getting sulphated zirconia, in air or in inert atmosphere, up to 4 hours depending on the precursor material used.

According to another aspect of the present invention there is provided a process for producing isopulegol-rich in l-isopulegol isomer, from d-citronellal comprising:

i. heating d-citronellal in the presence of a solvent to reflux temperature;
ii. adding shape selective acidic microporous solid catalyst such as hereindescribed in an amount of 2.5–3% by wt. of d-citronellal;
iii. maintaining the reaction at reflux temperature under stirring for 20–90 min preferably 20–40 min followed by
iv. recovering the desired isopulegol rich in l-isopulegol isomer by conventional methods.

The above process of the present invention provides a selective synthesis of l-isopulegol from d-citronellal using an improved catalyst which is combination of sulphated zirconia with microporous carbon molecular sieves (CMS) forming a composite material (i.e. CMS/S-ZrO2 material) with higher selectivity for the desired product l-isopulegol. The process of manufacture of improved coated sulphated zirconia catalyst (UDCaT 2) is as disclosed and described herein before. The catalyst used in the above process is sulphated zirconia based novel catalyst the preparation of which is disclosed and described herein before. The said UDCaT-2 catalyst comprised a synergistic combination of sulphated metal oxide and at least one carbon molecular sieve and optionally heteropoly acid and having pore volume in the range of 0.1–0.2 $m^3$/g and pore size distribution in the range of 25–40 Å.

According to yet another aspect of the present invention there is provided a process for mono nitration of aromatic compounds $C_6H_4R_1R_2$ wherein $R_1$=—$CH_3$, —$C_2H_5$, —Cl, —Br or —I and $R_2$=—H or —$CH_3$ comprising:

i. feeding said aromatic compound and acetic anhydride in the mole ratio of 2:5 to 1:10;

ii. adding modified sulphated zirconia catalyst such as herein described in an amount of 0.5% to 1.5% by weight/volume to the reaction mixture;

iii. adding conc. nitric acid in the mole ratio of 1:1 to 1:5 with respect to said aromatic compound to the reaction mixture by semi-batch mode and maintaining the reaction temperature between 20–30° C.

iv. quenching the reaction and thereafter;

v. recovering the mononitrated aromatic compound ($NO_2C_6H_4R$) from the reaction mixture by conventional methods.

The process of the present invention is particularly useful when the aromatic compound employed in step (i) is $C_6H_5R$, where R=—Cl (chlorobenzene) or R=—$CH_3$ (toluene).

The catalyst used in the above process is sulphated zirconia based novel catalysts whose preparation has described in our co-pending Indian application No. entitled "Process for preparation of shape selective acidic microporous solid catalysts-UDCaT-2". The process of manufacture of improved CMS coated sulphated zirconia catalyst (UIDCaT 2) is as disclosed and described herein before. The catalysts used in the process of the invention combined sulphated zirconia with microporous carbon molecular sieves (CMS) to form a composite material (i.e. a CMS/S-$ZrO_2$ material) which is shape selective with higher selectivity towards formation of the para- product. The said UDCaT-2 catalyst comprised a synergistic combination of sulphated metal oxide and at least one carbon molecular sieve and optionally heteropoly acid and having pore volume in the range of 0.1–0.2 $m^3$/g and pore size distribution in the range of 25–40 Å.

EXAMPLES

The invention, its objective and advantages, will now be illustrated by way of non-limiting examples. Examples are by way of illustration only and in no way restrict the invention.

I. ON CATALYST PREPARATION

The CMS modified sulphated zirconia catalysts are classified as UDCaT-2 type of catalysts. Chemicals used in these examples namely, zirconium oxychloride ($ZrOCl_2.8H_2O$), dodecatungstophosphoric acid ($H_3PO_4, 12WO_3.nH_2O$, molecular weight 2880.17), 25% ammonia solution (AR Grade) and solvents methanol, benzene, carbon tetrachloride, hexane, cyclohexane were obtained locally from s.d. Fine Chem. Ltd. All the solvents were of AR grade. Polyvinyl alcohol was obtained from Loba Chemie Ltd. (Degree of polymerization: 1700–1800)

EXAMPLE 1: Preparation of S-$ZrO_2$[650]

S-$ZrO_2$[650] was prepared by the conventional precipitation technique. About 110 g of zirconium oxychloride was dissolved in about 2000 ml of distilled water. This was then filtered to remove any impurities. The solution was then added dropwise simultaneously with 25% ammonia solution with constant stirring. On addition of both the solution white precipitate of zirconium hydroxide was obtained. The pH of the solution was maintained between 8–10. After complete precipitation, it was allowed to digest for 4 h. The precipitate was then washed and filtered through a Buchner funnel. The precipitate was washed and made free of chloride ions and ammonia, as verified from the phenolphthalein and the silver nitrate tests, respectively. This hydroxide was dried in an oven for 24 h at 110° C. The dried cake was then crushed to obtain the desired particle size.

Sulphation of this hydrous zirconia was carried out by percolating a 1N sulphuric acid solution through it taken as 15 ml/g of solid hydrous zirconia. The sulphated zirconium hydroxide was then calcined in air at 650° C. for 3 h in a quartz tube to yield the sulphated zirconia catalyst.

The catalyst thus obtained was having very good activity for the nitration of chlorobenzene as shown in our co-pending Indian Patent Application entitled "A process for selective nitration of aromatic compounds using UDCaT-2". The process of manufacture of improved coated sulphated zirconia catalyst (UDCaT 2) is as disclosed and described herein before. The catalyst has been further characterized by BET surface area, pore size distribution, pore volume, XRD, SEM and FTIR techniques. This catalyst was found to have a surface area of 100 $m^2$/g by BET method. The pore size of the catalyst was found to be 40 Å. The pore volume of the catalyst was found to be 0.107856 $cm^3$/g. SEM of the catalyst shows that the surface was quite smooth which indicates low surface area. For S-$ZrO_2$ the spectra shows a broad peak having shoulder peaks at 1218, 1152, 1066 and 1058 $cm^{-1}$, which are typical of a chelating bidentate sulfate ion coordinated to metal cation. This structure is stronger than that of usual metal sulphates and due to inductive effect of sulphur oxygen bonds, there is an increase in the Lewis acidity of the $Zr^{4+}$ metal cation. S-$ZrO_2$ is found to be crystalline in nature and shows a tetragonal structure as can be clearly seen from the XRD pattern. Table 1 gives the d/n and $I/I_o$ values for S-$ZrO_2$. The chemical analysis of the catalyst showed 3.8% w/w of sulphur.

TABLE 1

XRD analysis of S-$ZrO_2$ [650]

| 2θ | d/n (Å) | $I/I_o$ |
|---|---|---|
| 27.5 | 3.24 | 25 |
| 29.5 | 3.03 | 100 |
| 30.8 | 2.90 | 10 |
| 34.3 | 2.61 | 25 |
| 49.6 | 1.84 | 70 |
| 59.4 | 1.55 | 40 |

EXAMPLE 2: Preparation of Heteropoly Acid (HPA) on S-$ZrO_2$ (HPA/S-$ZrO_2$)

The HPA used in this study was dodecatungstophosphoric acid. 1 g HPA was dissolved in methanol and then impregnated on to 20 g S-$ZrO_2$, as in EXAMPLE 1, followed by drying in an oven at 120° C. for 24 h. This catalyst was then calcined in air at 250° C. for 3 h. The material thus obtained was HPA/S-$ZrO_2$. The x-ray diffraction pattern showed that the catalyst was crystalline in nature. The FTIR peaks in the region 1400–1700 $cm^{-1}$ indicate the phosphorous linkages that come by way of heteropoly acid deposition. The amount of phosphorous detected in the catalyst was found to be 0.09% w/w with traces of tungsten.

EXAMPLE 3: Preparation of CMS/S-$ZrO_2$

S-$ZrO_2$[650] catalyst was prepared as in EXAMPLE 1. This catalyst was then mixed with polyvinyl alcohol (PVA) solution (2 g dissolved in 25 ml distilled water at 90° C. with constant stirring) by incipient wetness technique. 2.5 g of sulphated zirconia required 1.3 ml of PVA solution. The mixture was then calcined in air preferably between 350° C. for 3 h. The material, thus obtained, was CMS/S-$ZrO_2$. The catalyst was further characterized by XRD, FTIR, SEM, BET surface area and pore volume. SEM showed that the surface of the catalyst was rough as compared to S-$ZrO_2$ which is probably due to the CMS coating on the catalyst. XRD analysis of the catalyst showed some additional peaks with respect to that obtained in S-ZrO$_2$. Table 2 shows the XRD results. Similar results were obtained from FTIR spectrum. The BET surface area of this catalyst was found to be 64.30 m$^2$/g. The average pore volume of the catalyst was found to be 0.165 m$^3$/g. The pore size distribution of the catalyst was found to be 29 Å. This catalyst was found to give very high selectivity towards the formation of para-product in the nitration reactions as described in our co-pending Indian Patent Application entitled, "A process for selective nitration of aromatic compounds using UDCaT-2". The catalyst consisted of 1.3% carbon, 0.5% hydrogen and about 1% sulphur.

TABLE 2

XRD analysis of CMS/S-ZrO$_2$

| 2θ | D/n (Å) | I/I$_o$ |
|---|---|---|
| 23.9 | 3.72 | 12.33 |
| 27.8 | 3.21 | 41.1 |
| 29.7 | 3.01 | 100 |
| 31.0 | 2.88 | 30.14 |
| 34.1 | 2.63 | 16.44 |
| 34.8 | 2.57 | 20.55 |
| 37.8 | 2.38 | 10.96 |
| 40.3 | 2.23 | 6.85 |
| 44.2 | 2.05 | 9.59 |
| 49.8 | 1.83 | 54.79 |
| 55.2 | 1.66 | 6.85 |
| 59.8 | 1.54 | 24.66 |

EXAMPLE 4: Preparation of CMS/HPA/S-ZrO$_2$

HPA/S-ZrO$_2$ catalyst was prepared as in EXAMPLE 2. This catalyst was then mixed with polyvinyl alcohol solution (2 g dissolved in 25 ml distilled water at 90° C. with constant stirring) by incipient wetness technique. The mixture was then calcined at 250° C. for 3 h in air. The material thus obtained was CMS/HPA/S-ZrO$_2$.

The catalysts in EXAMPLES 1–4 were found to be high in selectivity towards the formation of para- product as mentioned in the co-pending Indian Patent Application entitled "A process for selective nitration of aromatic compounds using UDCaT-2".

EXAMPLE 5: Preparation of Zirconia ZrO$_2$[230–350]

ZrO$_2$[230–350] was prepared by the conventional precipitation technique as in EXAMPLE 1 up to the stage of formation of zirconium hydroxide. This hydroxide was dried in an oven for 24 h at 110° C. The dried cake was then crushed to obtain the desired particle size. This was then calcined at 350° C. for 3 h.

EXAMPLE 6: Preparation of S-ZrO$_2$[230–350]

S-ZrO$_2$[230–350] was prepared by the conventional precipitation technique as in EXAMPLE 1 up to the stage of sulphation. The sulphated zirconium hydroxide was then calcined in air at 350° C. for 3 h in a quartz tube to yield the S-ZrO$_2$[230–350] catalyst. The catalyst has been characterized by BET surface area, pore size distribution, pore volume, XRD, FTIR and SEM techniques. This catalyst was found to have a surface area of 160 m$^2$/g by BET method. The pore size of the catalyst was found to be 28 Å. The pore volume of the catalyst was found to be 0.115436 cm$^3$/g. It was found to be crystalline in nature. The details of XRD analysis are given in Table 3. The SEM shows that the catalyst surface is smooth as compared to that of CMS/S-ZrO$_2$[230–350]. Here again the FTIR spectrum was found to be very similar to S-ZrO$_2$ except that the peaks were more found to be less intense as compared to S-ZrO$_2$. This can be attributed to the low calcination temperature hence the peaks were not well defined, but still retaining the nature of active site of the catalyst. The catalyst consisted of 4.2% sulphur.

TABLE 3

XRD analysis of S-ZrO$_2$ [230–350]

| 2θ | d/n (Å) | I/I$_o$ |
|---|---|---|
| 28.4 | 3.14 | 100 |
| 31.2 | 2.86 | 76.47 |
| 34.6 | 2.59 | 35.29 |
| 49.6 | 1.84 | 58.82 |

EXAMPLE 7: Preparation of CMS/S-ZrO$_2$[230–350]

S-ZrO$_2$[230–350] was prepared as explained in EXAMPLE 6. This catalyst was then mixed with polyvinyl alcohol (PVA) solution (2 g dissolved in 25 ml distilled water at 90° C. with constant stirring) by incipient wetness technique. 2.5 g of sulphated zirconia required 1.3 ml of PVA solution. The mixture was then calcined in air at 350° C. for 3 h. The material, thus obtained, was CMS/S-ZrO$_2$[230–350]. The catalyst has been characterized by BET surface area, pore size distribution, pore volume, XRD, FTIR, and SEM techniques. This catalyst was found to have a surface area of 145 m$^2$/g by BET method. The pore size of the catalyst was found to be 27 Å. The pore volume of the catalyst was found to be 0.108337 cm$^3$/g. It was found to be crystalline in nature from the XRD data and the details are given in Table 4. The SEM shows that the catalyst surface is rough as compared to S-ZrO$_2$[230–350]. This can be attributed to the CMS coating on S-ZrO$_2$[230–350]. The FTIR spectrum of CMS/S-ZrO$_2$[230–350] was found to be very similar to S-ZrO$_2$[230–350] indicating that the nature of active site has not changed even after coating S-ZrO$_2$[230–350] with CMS. The catalyst consisted of 1.3% carbon, 0.8% hydrogen and about 1% sulphur.

TABLE 4

XRD analysis of CMS/S-ZrO$_2$ [230–350]

| 2θ | d/n (Å) | I/I$_o$ |
|---|---|---|
| 30.5 | 2.93 | 100 |
| 35.4 | 2.53 | 18.52 |

This catalyst was found to be highly selective towards the formation of l-isopulegol from d-citronellal following selective cyclization of d-citronellal to l-isopulegol.

EXAMPLE 8–11: Preparation of CMS/Solvent/S-ZrO$_2$ [230–350]

In EXAMPLES 8–11 S-ZrO$_2$[230–350] was prepared as in EXAMPLE 6.

2.5 g of S-ZrO$_2$[230–350] was then soaked in a solvent, as shown in Table 1, to just wetness. This was then mixed with polyvinyl alcohol (PVA) solution (2 g dissolved in 25 ml distilled water at 90° C. with constant stirring) by incipient wetness technique. 2.5 g of sulphated zirconia required 1–1.5 ml of PVA solution. The mixture was then calcined in air at 350° C. for 3 h. The material, thus obtained, in each example is designated as shown in Table 1.

TABLE 1

Details of EXAMPLES 8–11

| EXAMPLE NO. | Solvent used for soaking S—ZrO$_2$[230–350] | Name of the product formed |
|---|---|---|
| 8 | Benzene | CMS/Benzene/S—ZrO$_2$[230–350] |
| 9 | Cyclohexane | CMS/Cyclohexane/S—ZrO$_2$[230–350] |
| 10 | Carbon tetrachloride | CMS/Carbon tetrachloride/S—ZrO$_2$[230–350] |
| 11 | Hexane | CMS/Hexane/S—ZrO$_2$[230–350] |

The products of these Examples have given better conversion (except that of EXAMPLE 10). However, in selectivity in cyclization of d-citronellal was slightly low over those Examples in which soaking in solvent is not done, catalyst of EXAMPLE 7 (CMS/S-ZrO$_2$,[230–350]).

EXAMPLE 12: Preparation of CMS[120]/S-ZrO$_2$[230–350]

S-ZrO$_2$[230–350] was prepared as explained in EXAMPLE 6. This was then mixed with polyvinyl alcohol (PVA) solution (2 g dissolved in 25 ml distilled water at 90° C. with constant stirring) by incipient wetness technique. 2.5 g of sulphated zirconia required 1.3 ml of PVA solution. The mixture was then dried in an oven at 120° C. for 3 h. The material, thus obtained, was CMS[120]/S-ZrO$_2$[230–350].

EXAMPLE 13: Preparation of CMS[230]/S-ZrO$_2$[230–350]

S-ZrO$_2$[230–350] was prepared as explained in EXAMPLE 6. This as then mixed with polyvinyl alcohol (PVA) solution (2 g dissolved in 25 ml distilled water at 90° C. with constant stirring) by incipient wetness technique. 2.5 g of sulphated zirconia required 1.3 ml of PVA solution. The mixture was then calcined at 230° C. for 3 h. The material, thus obtained, was CMS [230]/S-ZrO$_2$ [230–350].

Catalysts in EXAMPLES 12 and 13 were found to give selectivity as good as that of EXAMPLE 7, in the cyclization of d-citronellal, following selective cyclization of d-citronellal to l-isopulegol. However, higher carbonization temperature as that of EXAMPLE 7 is preferred to avoid danger of leaching of the CMS layer.

EXAMPLE 14: Preparation of CMS[250]/S-ZrO$_2$

S-ZrO$_2$[650] was prepared as explained in EXAMPLE 1. This was then mixed with polyvinyl alcohol (PVA) solution (2 g dissolved in 25 ml distilled water at 90° C. with constant stirring) by incipient wetness technique. 2.5 g of sulphated zirconia required 1.3 ml of PVA solution. The mixture was then calcined at 250° C. for 3 h. The material, thus obtained, was CMS[250]/S-ZrO$_2$.

Catalyst in EXAMPLE 14 was found to give the same conversion as that of EXAMPLE 3 but the latter is preferred to achieve high selectivity towards the formation of para-product in nitration of chlorobenzene and toluene following process for selective nitration of aromatic compounds.

CHARACTERIZATION OF CATALYSTS

Chemical Analysis

The results of chemical analysis of the sulphated zirconia catalysts prepared as explained in Examples 1, 3, 6 and 7 are shown in Table 5.

TABLE 5

| Catalyst | Example No. | Carbon (%) | Hydrogen (%) | Sulphur (%) |
|---|---|---|---|---|
| S-ZrO$_2$ [650] | 1 | — | — | 3.8 |
| CMS/S-ZrO$_2$ | 3 | 1.3 | 0.5 | 1.0 |
| S-ZrO$_2$ [230–350] | 6 | — | — | 4.2 |
| CMS/S-ZrO$_2$ [230–350] | 7 | 1.3 | 0.8 | 1.0 |

Surface Area Analysis

The sulphated zirconia catalysts prepared as explained in Examples 1, 3, 6 and 7 show that their BET surface area values are within the range of 60–165 m$^2$/g.

Pore Volume Analysis

Using nitrogen adsorption isotherm pore volume of the sulphated zirconia catalysts prepared as explained in Examples 1, 3, 6 and 7 was found to be in the range of 0.1–0.2 m$^3$/g.

Pore Size Distribution

The pore size distribution of the sulphated zirconia catalysts prepared as explained in Examples 1, 3, 6 and 7 was found to be in the range of 25–40 Å.

X-ray Diffraction (XRD) Technique

The d spacing of the sulphated zirconia catalysts prepared as explained in Examples 1, 3, 6 and 7 was determined and was found to be in the range of 1.5–3.75 Å for all the peaks. The d spacing for high intensity peaks was found to be in the range of 1.8–3.25 Å.

Fourier Transform Infra Red (FTIR) Technique

The FTIR spectrum was determined for the sulphated zirconia catalysts prepared as explained in Examples 1, 3, 6 and 7 and it was found that the patterns of the spectra of these catalysts were very similar which indicated that the morphology of the catalytic material was retained and was not affected by the carbon molecular sieve coating.

II. ON CYCLIZATION OF D-CITRONELLAL TO L-ISOPULEGOL WITH DIFFERENT CATALYSTS

EXAMPLES 15–24

5 g of citronellal and 15 g of toluene were taken in a 100 ml fully baffled glass reactor. The reaction mixture was maintained at 95° C. under stirring. 5 g of one of the acidic microporous catalysts (as shown in Table 6 below), prepared as above in EXAMPLES 1, 5 to 13 described above was added to the reaction mixture. The reaction was monitored by gas chromatography (GC) and the conversion and selectivity were calculated. The reaction was carried out for the required period as delineated in Table 6. The conversion and selectivity at the end of the reaction are also given in Table 6. The formation of l-isopulegol was established by its boiling point, comparison of GC-MS of l-isopulegol with the authentic product and polarography.

TABLE 6

Cyclization of d-citronellal using solid acid catalysts

| Example No. | Catalysts | Reaction Time (min) | Conversion of d-citronellal (%) | Selectivity for 1-isopulegol (%) |
|---|---|---|---|---|
| 15 | Example 5 | 90 | 0 | — |
| 16 | Example 6 | 10 | 96 | 46 |
| 17 | Example 1 | 05 | 95 | 35 |

TABLE 6-continued

Cyclization of d-citronellal using solid acid catalysts

| Example No. | Catalysts | Reaction Time (min) | Conversion of d-citronellal (%) | Selectivity for l-isopulegol (%) |
|---|---|---|---|---|
| 18 | Example 7 | 30 | 91 | 65 |
| 19 | Example 8 | 20 | 95 | 52 |
| 20 | Example 9 | 20 | 96 | 61 |
| 21 | Example 10 | 30 | 88 | 53 |
| 22 | Example 11 | 20 | 95 | 58 |
| 23 | Example 12 | 90 | 91 | 71 |
| 24 | Example 13 | 30 | 95 | 65 |

As seen from the above table the reaction of Example 15 did not proceed where catalyst was $ZrO_2$[230–350]. In Examples 18, 23 and 24, the process where CMS[120]/S-$ZrO_2$[230–350], CMS[230]/S-$ZrO_2$[230–350] and CMS/S-$ZrO_2$[230–350] were used as catalysts, respectively, the reaction was slow but selectivity towards the formation of l-isopulegol was very high as compared to that obtained in process of Examples 16 and 17 where S-$ZrO_2$[230–350] and S-$ZrO_2$[650] were used as catalysts, respectively, wherein the reaction rates were higher but the selectivities were poor. In Examples 19–22 which were also carried out in accordance with the invention but where the catalysts were prepared by soaking sulphated zirconia with different organic solvents before coating showed reduced selectivity as compared to EXAMPLES 18, 23 and 24.

The process of present invention showed best performance in Example 18 using CMS/S-$ZrO_2$[230–350] as catalyst as the catalyst can be reused without the danger of leaching of the CMS layer around the active catalyst. This is also possible in case of CMS[120]/S-$ZrO_2$[230–350] and CMS[230]/S-$ZrO_2$[230–350] as the polymer is not sufficiently carbonized. Also the increase in the selectivity towards the formation of l-isopulegol by these catalysts can be attributed to the presence of CMS layer which acts as a barrier for the bulkier ether molecules which are formed as by-products during the cyclization.

III. ON SELECTIVE NITRATION OF AROMATIC COMPOUNDS

EXAMPLE 25: Mono nitration of chlorobenzene with S-$ZrO_2$[650]

0.2 gmol of chlorobenzene and 0.5 gmol of acetic anhydride (1:2.5) were taken in a glass reactor. 2.24 g of S-$ZrO_2$[650] catalysts was prepared as detailed herein before under EXAMPLES 1 to 4 and 14.

The thus prepared catalyst was added to this reaction mixture. 70% nitric acid was pumped in the reactor at a constant rate of $1.85 \times 10^{-5}$ gmol/sec to 78 ml of the organic phase. The reaction was carried out at 28° C. in a water bath. In this reaction since acetic anhydride was taken in excess it shifts the equilibrium towards the formation of acetyl nitrate in liquid phase. It is this acetyl nitrate which takes part in the nitration of chlorobenzene. The reaction was carried out in a 5 cm long flat bottom glass-lined reactor of 3 cm internal diameter equipped with four baffles and a six pitched bladed turbine placed at 0.5 cm from the bottom. Samples were withdrawn from the reactor at regular intervals of time. Nitric acid, acetic anhydride and acetyl nitrate were extracted with water when two layers were formed. The bottom layer was found to be the organic phase which was treated with anhydrous sodium sulphate to remove any traces of the dissolved acid, acetic anhydride and acetyl nitrate.

Samples were analyzed on a Chemito Gas Chromatograph (GC) equipped with a flame ionization detector. A stainless steel column 2 m long with 3 mm internal diameter packed with AT-1000 was used for the analysis. The carrier gas used was nitrogen at the flow rate of 30 ml/min. The oven temperature was maintained at 150° C. for 6 min. The injector and detector temperatures were maintained at 300° C.

Example 26–29: Mono nitration of chlorobenzene with and without

In EXAMPLES 26–29 the process of EXAMPLE 25 was repeated except that in EXAMPLE 26 no catalyst was used, in EXAMPLES 27–29 catalysts, prepared as detailed herein before under EXAMPLES 1 to 4 and 14 were used as given in Table 7 below. The samples were analyzed as in EXAMPLE 25. The percentage conversion and o:p ratio in respect of each example has been delineated in TABLE 7. Since EXAMPLE 27 showed best results in nitration of chlorobenzene we have processed the product further to study the yield quantitatively.

In EXAMPLE 27, at the end of the reaction, the unreacted chlorobenzene was removed by distillation of the recovered crude product at 132° C. The total weight of the product was then found to be 6.2 g (theoretical 7.9 g). This mixture consisted of 93% p-nitrochlorobenzene and 7% o-nitrochlorobenzene. No meta-isomer was obtained.

TABLE 7

Nitration of Chlorobenzene

| Example No. | Solid Catalyst | Conversion of $HNO_3^{\#}$(%) | o:p Selectivity~ |
|---|---|---|---|
| 25 | S-$ZrO_2$ [650] | 47 | 1:10.6 |
| 26 | No catalyst | 0 | — |
| 27 | CMS/S-$ZrO_2$ | 45 | 1:13.2 |
| 28 | HPA/S-$ZrO_2$ | 41 | 1:8.6 |
| 29 | CMS/HPA/S-$ZrO_2$ | 21 | 1:10.2 |

Immediately after the addition of nitric acid was complete.

It will be seen from Table 7 that process of EXAMPLE 27 gives best o:p ratio, with percentage conversion almost the same as in EXAMPLE 25.

B. Nitration of Toluene

In the classical nitration of toluene with the mixture of sulphuric acid and nitric acid o:p ratio of 1:0.6 has been reported. In the following examples (EXAMPLES 30–34) mono nitration of toluene has been described.

EXAMPLE 30–34: Nitration of toluene with and without catalyst

In EXAMPLES 30–34 the process of EXAMPLE 25 was repeated using toluene instead of chlorobenzene and at 20° C. instead of 28° C. and that in EXAMPLE 30 no catalyst was used, in EXAMPLE 32 a known catalyst was used and in EXAMPLES 31,33 and 34 catalysts, prepared as detailed herein before under EXAMPLES 1 to 4 and 14. The catalysts used are shown in Table 8. When catalyst was used it was 0.92 g and all the reactions were carried out at 20° C. The reaction was monitored by GC as in EXAMPLE 25. Conversions and o:p selectivities obtained in each example are given in Table 8. Since EXAMPLE 34 showed best results in nitration of toluene we have processed the product further to study the yield quantitatively.

In EXAMPLE 34, at the end of the reaction, the unreacted toluene was removed by distillation of the recovered crude product at 110° C. The total weight of the product was then found to be 11.2 g (theoretical 13.7 g). This mixture consisted of 45% p-nitrotoluene, 51% o-nitrotoluene and 4% m-nitrotoluene.

TABLE 8

Various Catalysts used for the Nitration of Toluene

| Example No. | Catalyst | Conversion of $HNO_3^{\#}$(%) | o:p Selectivity⁻ |
|---|---|---|---|
| 30 | No catalyst | 60 | 1:0.55 |
| 31 | S-ZrO$_2$ | 96 | 1:0.70 |
| 32 | DTP/K-10* | 90 | 1:0.65 |
| 33 | CMS [250]/S-ZrO$_2$ | 96 | 1:0.75 |
| 34 | CMS/S-ZrO$_2$ | 98 | 1:0.86 |

Immediately after the addition of nitric acid was complete.
⁻In all the experiments 1–1.5% of meta isomer was found.
*DTP (dodecatungstophosphoric acid) supported on K-10 clay is a well known solid acid catalyst developed by G.D. Yadav and N. Kirthivasan, J. Chem. Soc. Chem. Commun., 3, (1995), 203–204.

As seen from the above tables (Tables 7 and 8) in both. the mono nitration of chlorobenzene and toluene, CMS/S-ZrO$_2$ was found to give the highest selectivity for the para-product formation as compared to other catalysts which are non-shape selective. This can be attributed to the carbon molecular sieve barrier over sulphated zirconia which allows the formation of more linear para- product as compared to the bulkier ortho- and meta-products.

We claim:

1. An active highly acidic microporous solid catalyst comprising sulphated metal oxide coated with carbon molecular sieves and optionally heteropoly acid and having pore volume in the range of 0.1–0.2 m³/g and pore size distribution in the range of 25–40 Å.

2. An active highly acidic microporous solid catalyst as claimed in claim 1 wherein said sulphated metal oxide and said carbon molecular sieve coating have a BET surface area in the range of 60–165 m²/g, pore volume in the range of 0.1 to 0.2 m³/g, and pore size distribution in the range of 25–40 Å and d-spacing in the range of 1.5 to 3.75 Å for all the peaks.

3. An active highly acidic microporous solid catalyst as claimed in claim 1 wherein said carbon molecular sieve is selected from polyfurfuryl alcohol, phenol-formaldehyde resin, polyvinyl alcohol, and polyacrylo nitrile.

4. A process for producing an active highly acidic microporous solid catalyst as claimed in claim 1 comprising:
   i. providing sulphated zirconia, said sulphated zirconia optionally wetted with solvent;
   ii. coating the sulphated zirconia with at least one carbon molecular sieve modifying agent/precursors selected from polyfurfuryl alcohol, phenol-formaldehyde resin, polyvinyl alcohol, and polyacrylo nitrile and optionally heteropoly acid;
   iii. drying the carbon molecular sieve precursor coated sulphated zirconia at a temperature between 100–150° C.;
   iv. calcining the carbon molecular sieve precursor coated sulphated zirconia at a temperature up to 350° C. to thereby obtain the sulphated zirconia in the form of shape selective microporous solid catalyst.

5. A process for producing an active highly acidic microporous solid catalyst as claimed in claim 4 wherein the solvent used for wetting the sulphated zirconia is selected from aliphatic, aromatic, cyclic or chlorinated hydrocarbons, aliphatic alcohols, and aliphatic ketones.

6. A process for producing an active highly acidic microporous solid catalyst as claimed in claim 4 wherein the heteropoly acid used is dodecatungstophosphoric.

7. An active highly acidic microporous solid catalyst as claimed in claim 2, wherein said sulphated metal oxide and said carbon molecular sieve coating have a d-spacing in the range of 1.8–3.25 Å for high intensity peaks.

8. A process as in claim 4, wherein said calcining is carried out at between 100° C. and 350° C.

9. A process as claimed in claim 4 wherein the solvent used for wetting the sulphated zirconia is selected from carbon tetrachloride, benzene, cyclohexane and hexane.

10. A process for producing isopulegol-rich in l-isopulegol isomer, from d-citronellal using an active highly acidic microporous solid catalyst comprising sulphated metal oxide coated with carbon molecular sieves and optionally heteropoly acid and having pore volume in the range of 0.1–0.2 m³/g and pore size distribution in the range of 25–40 Å, said process comprising:
   i. heating d-citronellal in the presence of a solvent to reflux temperature;
   ii. adding said acidic microporous solid catalyst in an amount of 2.5–3% by wt. of d-citronellal;
   iii. maintaining the reaction at reflux temperature under stirring for 20–90 min followed by
   iv. recovering the desired isopulegol rich in l-isopulegol isomer.

11. A process as claimed in claim 10 wherein the solvent used is toluene.

12. A process as claimed in claim 10 wherein said catalyst is reused.

13. A process for mononitration of aromatic compounds $C_6H_4R_1R_2$ wherein
   $R_1$=—$CH_3$, —$C_2H_5$, —Cl, —Br or —I and
   $R_2$=—H or —$CH_3$ using as catalyst an active highly acidic microporous solid catalyst comprising sulphated metal oxide coated with carbon molecular sieves and optionally heteropoly acid and having pore volume in the range of 0.1–0.2 m³/g and pore size distribution in the range of 25–40 Å, said process comprising:
   i. feeding said aromatic compound and acetic anhydride at a ratio of 2:5 to 1:10 (mole ratio);
   ii. adding said catalyst in an amount of 0.5 to 1.5% by weight/volume to the reaction mixture;
   iii. adding conc. nitric acid in the mole ratio of 1:1 to 1:5 with respect to said aromatic compound to the reaction mixture by semi-batch mode and maintaining the reaction temperature between 20–30° C.;
   iv. quenching the reaction and thereafter;
   v. recovering the mononitrated aromatic compound ($NO_2C_6H_4R$) from the reaction mixture.

14. A process as claimed in claim 13 wherein said aromatic compound used is selected from $C_6H_5R$, R=—Cl (chlorobenzene), $C_6H_5R$, R=—$CH_3$ (toluene).

* * * * *